US00PP20082P2

(12) United States Plant Patent
Bloom

(10) Patent No.: US PP20,082 P2
(45) Date of Patent: Jun. 9, 2009

(54) ***CAMPANULA* PLANT NAMED 'BLUE RIVULET'**

(50) Latin Name: *Campanula poscharskyana*
Varietal Denomination: Blue Rivulet

(76) Inventor: Adrian Bloom, Foggy Bottom, Bressingham, Diss, Norfolk IP22 2AB (GB)

( * ) Notice: Subject to any disclaimer, the term of this patent is extended or adjusted under 35 U.S.C. 154(b) by 0 days.

(21) Appl. No.: 12/156,720

(22) Filed: Jun. 3, 2008

(51) Int. Cl.
*A01H 5/00* (2006.01)

(52) U.S. Cl. ..... Plt./414
(58) Field of Classification Search ..... Plt./414
See application file for complete search history.

*Primary Examiner*—Annette H Para
(74) *Attorney, Agent, or Firm*—C. A. Whealy

(57) ABSTRACT

A new and distinct cultivar of *Campanula* plant named 'Blue Rivulet', characterized by its compact and outwardly spreading to trailing plant habit; freely branching habit; freely flowering habit; and violet blue-colored star-shaped flowers with lighter colored centers.

1 Drawing Sheet

Botanical designation: *Campanula poscharskyana.*
Cultivar denomination: 'Blue Rivulet'.

BACKGROUND OF THE INVENTION

The present invention relates to a new and distinct cultivar of *Campanula,* botanically known as *Campanula poscharskyana* and hereinafter referred to by the name 'Blue Rivulet'.

The new *Campanula* originated from an open-pollination of the *Campanula poscharskyana* 'Camgood', disclosed in U.S. Plant Pat. No. 13,161, as the female, or seed, parent with an unknown selection of *Campanula poscharskyana,* as the male, or pollen, parent. The new *Campanula* was discovered and selected by the Inventor as a single flowering plant from within the progeny of the stated open-pollination grown in a controlled outdoor nursery environment in Bressingham, United Kingdom in 2000.

Asexual reproduction of the new *Campanula* by cuttings in Bressingham, United Kingdom, since July, 2000, has shown that the unique features of this new *Campanula* are stable and reproduced true to type in successive generations.

SUMMARY OF THE INVENTION

Plants of the new *Campanula* have not been observed under all possible environmental conditions. The phenotype may vary somewhat with variations in environment such as temperature and light intensity without, however, any variance in genotype.

The following traits have been repeatedly observed and are determined to be the unique characteristics of 'Blue Rivulet'. These characteristics in combination distinguish 'Blue Rivulet' as a new and distinct cultivar:

1. Compact and outwardly spreading to trailing plant habit.
2. Freely branching habit.
3. Freely flowering habit.
4. Violet blue-colored star-shaped flowers with lighter colored centers.

Plants of the new *Campanula* differ from plants of the female parent, 'Camgood', in the following characteristics:

1. Plants of the new *Campanula* have shorter flowering stems than plants of 'Camgood'.
2. Plants of the new *Campanula* produce flowering stems all over the plant whereas plants of 'Camgood' only produce flowering stems towards the outside of the plant.
3. Plants of the new *Campanula* and 'Camgood' differed slightly in flower color.

Plants of the new *Campanula* can be compared to plants of the *Campanula* 'Emerald', disclosed in U.S. Plant Pat. No. 18,343. In side-by-side comparisons, plants of the new *Campanula* differed from plants of the 'Emerald' in the following characteristics:

1. Plants of the new *Campanula* were more compact and not as upright as plants of 'Emerald'.
2. Plants of the new *Campanula* had shorter and broader leaves than plants of 'Emerald'.
3. Plants of the new *Campanula* had darker-colored flowers than plants of 'Emerald'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Campanula.*

The photograph at the bottom of the sheet comprises a side perspective view of a typical flowering plant of 'Blue Rivulet' grown in a container.

The photograph at the top of the sheet is a close-up view of typical flowers and leaves of 'Blue Rivulet'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the winter and early spring in a polyethylene-covered greenhouse in Lancaster, Pa. for five months. During the production of the plants, day temperatures ranged from 18° C. to 27° C. and night temperatures averaging 18° C.

Botanical classification: *Campanula poscharskyana* 'Blue Rivulet'.

Parentage:

*Female parent.*—*Campanula poscharskyana* 'Camgood', disclosed in U.S. Plant Pat. No. 13,161.

*Male parent.*—Unknown selection of *Campanula poscharskyana,* not patented.

Propagation:

*Type.*—By cuttings.

*Time to initiate roots.*—About ten days at 20° C. to 25° C.

*Time to produce a rooted young plant.*—About 30 days at 20° C. to 25° C.

*Root description.*—Fine, fibrous; greyed white in color.

*Rooting habit.*—Freely branching; dense.

Plant description:

*Form.*—Herbaceous perennial. Compact and outwardly spreading to trailing plant habit; freely branching habit; vigorous growth habit. Campanulate flowers arranged in terminal and axillary clusters.

*Plant height.*—About 16 cm.

*Plant width.*—About 37 cm.

*Lateral branch description.*—Quantity per plant: About 15 primary branches each with numerous lateral branches. Length: About 27 cm. Diameter: About 3.5 mm. Internode length: About 1.5 cm to 2 cm. Strength: Strong. Texture: Smooth, glabrous. Color: Close to 137A.

Foliage description:

*Arrangement.*—Alternate, simple.

*Length.*—About 4.6 cm.

*Width.*—About 4.2 cm.

*Shape.*—Elliptical to cordate.

*Apex.*—Acute.

*Base.*—Acute to cordate.

*Margin.*—Irregularly crenate.

*Texture, upper and lower surfaces.*—Smooth, glabrous.

*Venation pattern.*—Pinnate; arcuate.

*Color.*—Developing foliage, upper and lower surfaces: Close to 137B. Fully expanded foliage, upper surface: Close to N137A; venation, 137C. Fully expanded foliage, lower surface: Close to 137C; venation, close to 137C.

*Petiole length.*—About 7.7 cm.

*Petiole diameter.*—About 2 mm.

*Petiole texture, upper and lower surfaces.*—Smooth, glabrous.

*Petiole color, upper and lower surfaces.*—Close to 137D.

Flower description:

*Flower arrangement and shape.*—Single campanulate star-shaped flowers arranged in terminal and axillary clusters; flowers face outwardly to upright. Freely flowering, about 30 flowers per lateral branch.

*Natural flowering season.*—Continuous flowering from late May until mid-summer in Pennsylvania.

*Flower longevity on the plant.*—About five to seven days; flowers persistent.

*Fragrance.*—None detected.

*Flower buds.*—Length: About 1.3 cm. Diameter: About 5 mm. Shape: Oblong. Color: Close to 90B.

*Flowers.*—Diameter: About 3.8 cm. Depth (height): About 2 cm.

*Petals.*—Arrangement: Five in a single whorl; fused. Length: About 1.8 cm. Width: About 7 mm. Shape: Elliptical. Apex: Acute. Margin: Entire. Texture, upper and lower surfaces: Smooth, glabrous; velvety. Color: When opening, upper surface: Close to 90B. When opening, lower surface: Close to 90D. Fully opened, upper surface: Towards the apex, close to 90C; center, close to 90D; towards the base, close to 85C; midvein, close to 90A. Fully opened, lower surface: Close to 90D; venation, similar to lamina.

*Sepals.*—Arrangement: Five in a single whorl; fused. Length: About 1.1 cm. Width: About 3 mm. Shape: Narrowly lanceolate. Apex: Acuminate. Margin: Entire. Texture, upper and lower surfaces: Smooth, glabrous. Color, upper and lower surfaces: Close to 146B.

*Peduncles.*—Length: About 2.2 cm. Diameter: About 1 mm. Aspect: About 30° from vertical. Strength: Strong. Texture: Smooth, glabrous. Color: Close to 146B.

*Reproductive organs.*—Stamens: Quantity per flower: Five. Anther shape: Narrowly lanceolate. Anther length: About 3 mm. Anther color: Close to 155A. Filament length: About 2.5 mm. Filament color: Close to N155D. Pollen amount: Scarce to moderate. Pollen color: Close to 155A. Pistils: Quantity per flower: One. Pistil length: About 1.7 cm. Stigma shape: Narrowly lanceolate and becoming three-parted with development. Stigma color: Close to 90B. Style length: About 1 cm. Style color: Close to 90C to 90D. Ovary color: Close to 157C.

*Seed/fruit.*—Seed and fruit production has not been observed.

Disease/pest resistance: Plants of the new *Campanula* have not been noted to be resistant to pathogens and pests common to *Campanula*.

Garden performance: Plants of the new *Campanula* have exhibited good tolerance to rain and wind and have been observed to be suitable for USDA Zones 4 to 7.

It is claimed:

1. A new and distinct *Campanula* plant named 'Blue Rivulet' as illustrated and described.

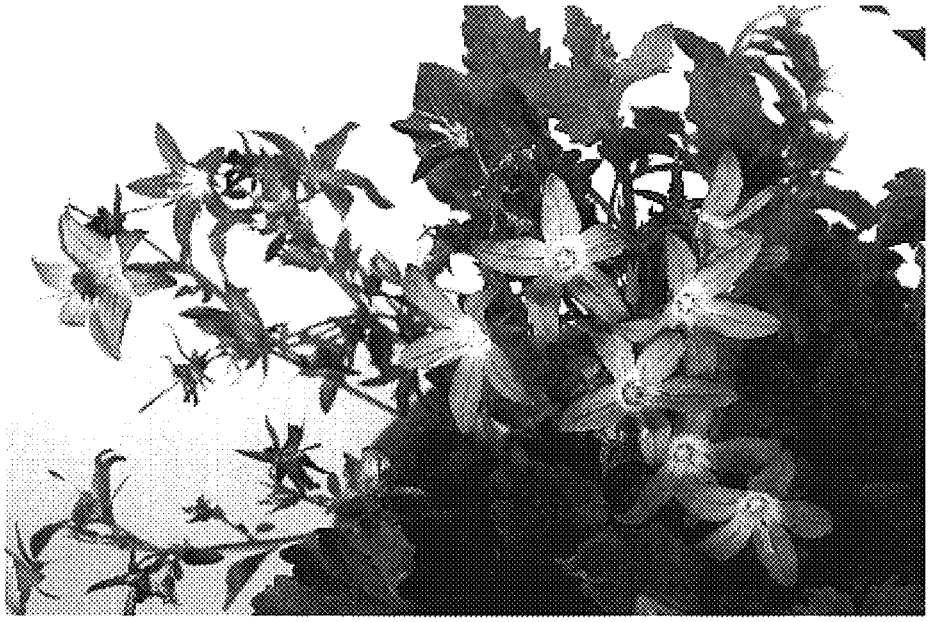
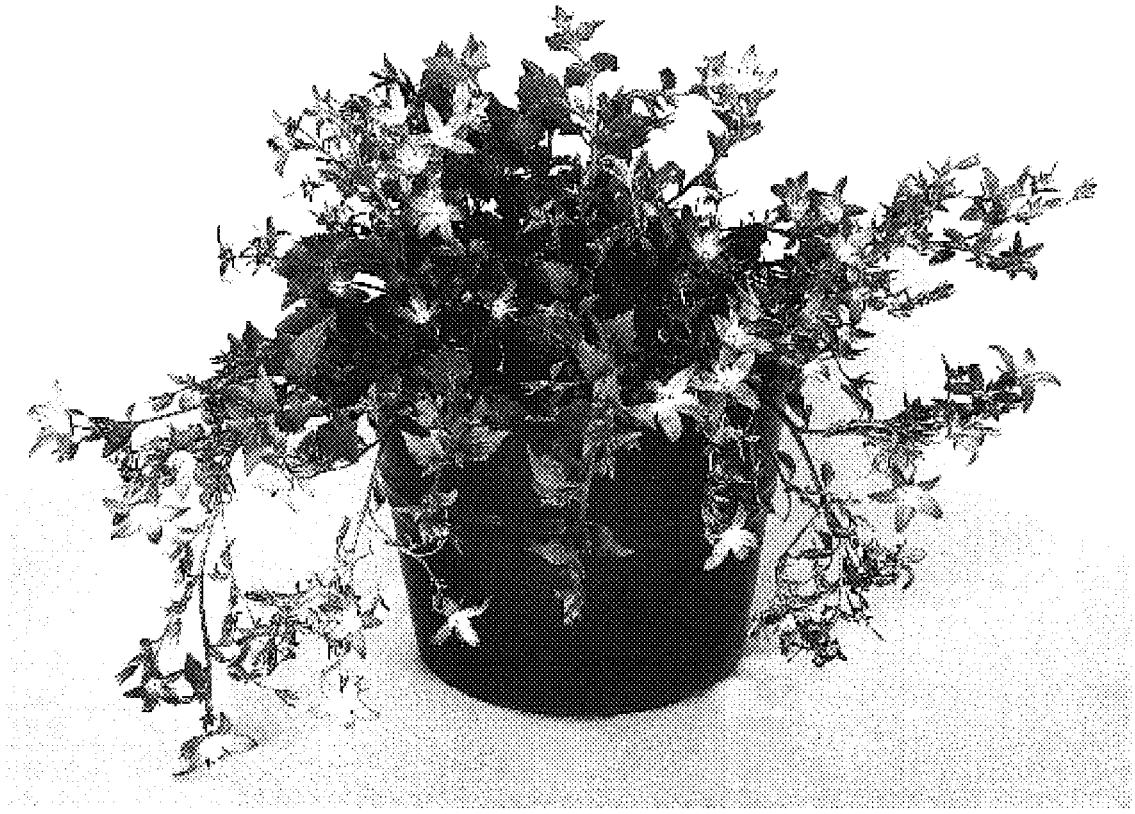

* * * * *